United States Patent [19]
Yoon

[11] Patent Number: 5,334,199
[45] Date of Patent: Aug. 2, 1994

[54] LIGATING INSTRUMENT AND METHODS OF LIGATING TISSUE IN ENDOSCOPIC OPERATIVE PROCEDURES

[76] Inventor: InBae Yoon, 2101 Highland Ridge Dr., Phoenix, Md. 21131

[21] Appl. No.: 930,320

[22] Filed: Aug. 17, 1992

[51] Int. Cl.$^5$ .................................................. A61B 17/00
[52] U.S. Cl. ........................................ 606/144; 606/139
[58] Field of Search ............... 606/139, 144, 146, 148, 606/151, 170, 171

[56] References Cited

U.S. PATENT DOCUMENTS

| | | |
|---|---|---|
| 2,227,270 | 12/1940 | Moore . |
| 2,610,631 | 9/1952 | Calicchio .......................... 606/139 |
| 2,856,933 | 10/1958 | Hildebrand et al. . |
| 3,033,204 | 5/1962 | Wood ................................ 606/139 |
| 3,580,256 | 5/1971 | Wilkinson et al. . |
| 3,871,379 | 3/1975 | Clarke . |
| 4,018,229 | 4/1977 | Komiya ............................. 606/139 |
| 4,345,599 | 8/1982 | McCarrell . |
| 4,592,355 | 6/1986 | Antebi ............................... 606/144 |
| 4,712,547 | 12/1987 | Bonnet ............................. 606/170 |
| 4,729,374 | 3/1988 | Alfranca ............................ 606/171 |
| 4,760,848 | 8/1988 | Hasson . |
| 4,923,461 | 5/1990 | Caspari et al. . |
| 4,935,027 | 6/1990 | Yoon . |
| 5,129,912 | 7/1992 | Noda et al. . |
| 5,133,723 | 7/1992 | Li et al. . |
| 5,196,022 | 3/1993 | Bilweis ............................. 606/148 |
| 5,242,459 | 9/1993 | Buelna . |

FOREIGN PATENT DOCUMENTS 0630693 10/1949 United Kingdom ............... 606/146

*Primary Examiner*—Stephan C. Pellegrino
*Assistant Examiner*—Jeffrey A. Schmidt

[57] ABSTRACT

A ligating instrument includes a handle for securing a proximal end of a ligating device externally of the body with one hand, the ligating device defining a lumen for passage therethrough of a length of ligature material formed with a ligature loop for being disposed externally of a distal end of the ligating device to be positioned around anatomical tissue to be ligated within the body, and an operating member coupled with the ligature material for being manually moved with the same hand as that securing the ligating device proximal end to pull the ligature material through the ligating device to form a ligature with the ligature loop in the anatomical tissue. A method of ligating tissue in endoscopic operative procedures includes the steps of securing a proximal end of a ligating instrument externally of the body with one hand, introducing a distal end of the ligating instrument at a surgical site in the body through a portal formed in tissue of the body, placing a length of ligature material carried by the ligating instrument around anatomical tissue to be ligated, moving an operating member of the ligating instrument with the same hand as that securing the proximal end to pull the ligature material through the ligating instrument to tighten the ligature material around the anatomical tissue to form a ligature and actuating a cutter of the ligating instrument to cut the ligature material away from the ligature.

17 Claims, 13 Drawing Sheets

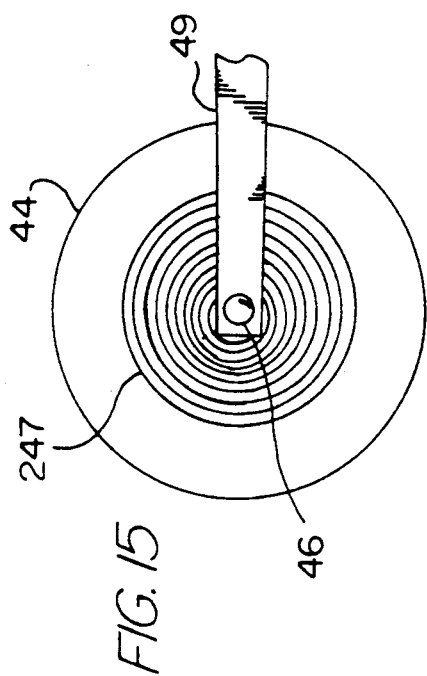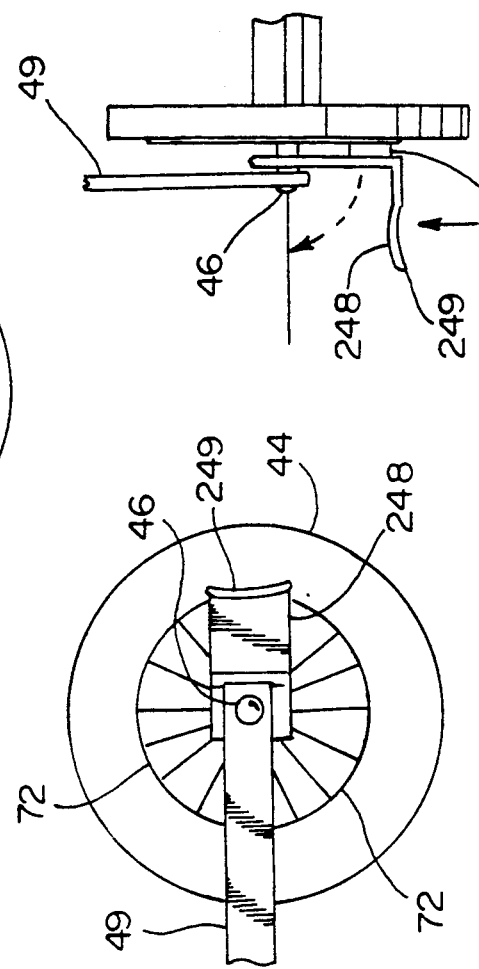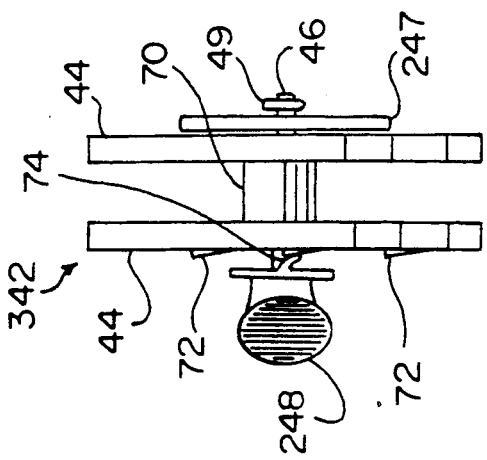

LIGATING INSTRUMENT AND METHODS OF LIGATING TISSUE IN ENDOSCOPIC OPERATIVE PROCEDURES

BACKGROUND OF THE INVENTION

1. Field of the Invention

The present invention pertains to ligating instruments and, more particularly, to ligating instruments particularly useful in endoscopic operative procedures to ligate anatomical tissue and methods of ligating anatomical tissue in endoscopic operative procedures.

2. Discussion of the Prior Art

Closed, or endoscopic, surgery, also known as least-invasive surgery, has become extremely popular for use in conducting many various procedures such as, for example, laparoscopy (pelviscopy), gastroentroscopy, laryngobronchoscopy and arthroscopy. In endoscopic operative procedures, access to surgical sites in the body is gained through portals of minimal size formed in tissue of the body to allow instruments to be introduced at the surgical sites via the portals. Endoscopic surgery provides many benefits over open surgery, which typically requires skin incisions of substantial size, including minimal invasiveness and trauma, avoidance of complications due to surgery, greatly reduced wound healing times, patient discomfort and hospitalization and rehabilitation times and concomitant cost savings associated with shorter hospital stays and performing surgery without general anesthesia and in non-hospital or out-patient surgery sites. Ligating anatomical tissue is a time consuming and tedious part of both endoscopic and open operative procedures due to the difficulty involved in applying an occluding ligature in anatomical tubular or non-tubular tissue or organ structure as is desirable in occluding or tying organ and tissue structure in many various procedures. Ligating anatomical tissue is particularly difficult in endoscopic surgery due to the limited room for maneuverability at the surgical site and the complicated operative steps required; and, accordingly, the advantages of endoscopic surgery are sometimes outweighed by the disadvantages caused by the length of time required to perform endoscopic procedures where such time is significantly extended due to the time required for ligation. Because endoscopic surgery is greatly preferred over open surgery, much effort has been spent to develop techniques for facilitating tissue ligation. One technique involves the use of ligating devices such as, for example, the Endoloop TM manufactured by Ethicon, Inc. Such ligating devices typically include an elongate tubular member defining a lumen for passage therethrough of a length of ligature material, the ligature material having an end secured to a proximal end of the tubular member. A portion of the ligature material disposed externally of a distal end of the tubular member is formed as a ligature loop, the loop being made by passing the ligature material through a knot formed in an end of the ligature material externally of the tubular member distal end. In use, the tubular member distal end is introduced, typically via a portal sleeve, at a surgical site in the body through a portal of minimal size formed in tissue of the body, with the proximal end of the tubular member held and secured externally of the body. The ligature loop is positioned around tissue to be ligated within the body; and, once the tissue is properly positioned within the loop, the tubular member is broken or fractured to break off or separate the proximal end from the remainder thereof. The ligature material can then be pulled, via the broken off proximal end, through the lumen of the tubular member while the knot, which is larger than the lumen at the tubular member distal end, remains held externally of the distal end such that the loop is reduced or tightened around the tissue to form a ligature. Once the ligature is formed, a surgical instrument introduced at the surgical site from another portal is used to cut the ligature material away from the knot leaving the ligature in place. The ligating devices require use of both of the surgeon's hands, one hand to hold the tubular member externally of the body and the other to break off the proximal end and pull the ligature material therewith while the one hand continues to hold the tubular member. Forming ligatures in endoscopic operative procedures in accordance with the ligating devices is tedious and time consuming due to the number and complexity of the procedural steps involved.

SUMMARY OF THE INVENTION

Accordingly, it is a primary object of the present invention to overcome the aforementioned disadvantages of prior art ligating devices and methods of ligating anatomical tissue in endoscopic operative procedures.

Another object of the present invention is to provide a ligating instrument for use in combination with presently available ligating devices to allow the ligating devices to be operated with one hand.

A further object of the present invention is to provide a ligating instrument having a length of ligature material extending therethrough for forming a ligature in anatomical tissue and a cutter mounted thereon for cutting the ligature material upon formation of a ligature with the ligating instrument.

A still further object of the present invention is to provide a ligating instrument having a movable operating member for drawing ligature material through the ligating instrument to tighten a ligature loop around anatomical tissue and relatively movable handle members operated by squeezing action to obtain additional tightening of the ligature loop with controlled tension.

Yet another object of the present invention is to provide a ligating instrument with a loop forming member at a distal end thereof to perform the function of a ligature knot and to permit ligature material to be drawn through the ligating instrument in a single direction only.

An additional object of the present invention is to provide a ligating instrument for use with a ligating device having a proximal end securing a length of ligature material, the ligating instrument including a movable operating member for automatically breaking off the proximal end of the ligative device from the remainder thereof to draw the ligature material through the ligating device in response to manual movement of the operating member.

It is also an object of the present invention to provide a ligating instrument having relatively movable handle members for drawing ligature material through the ligating instrument to form a ligature in anatomical tissue and a frangible portion on the ligating instrument for preventing relative movement of the handle members and for permitting relative movement of the handle members when the frangible portion is broken.

The present invention has as another object to provide a ligating instrument having a locking mechanism for preventing and selectively permitting movement of a movable cutter of the ligating instrument.

A further object of the present invention is to provide a ligating instrument having an operating member biased to draw ligature material through the ligating instrument to tighten the ligature material around anatomical tissue and a release mechanism for releasing the operating member to automatically draw the ligature material through the ligating instrument due to the bias.

An additional object of the present invention is to provide a ligating instrument having a movable operating member for moving ligature material through the ligating instrument to increase the size of a ligature loop in the ligature material to allow the ligature loop to be positioned around anatomical tissue and to reduce the size of the loop around the tissue in response to movement of the operating member.

A still further object of the present invention is to provide a ligating instrument for increasing the size of a ligature loop in a length of ligature material in response to manual movement of an operating member and automatically reducing the size of the ligature loop in response to movement of the operating member by a bias device.

Another object of the present invention is to provide a method of ligating anatomical tissue in endoscopic operative procedures including securing a ligating instrument with one hand externally of the body, moving an operating member of the ligating instrument with the one hand to draw ligature material through the ligating instrument to tighten the ligature material around tissue to form a ligature and actuating a cutter of the ligating instrument to cut the ligature material away from the ligature.

Some of the advantages of the present invention are that operation of presently available ligating devices is simplified and facilitated, the time required to ligate anatomical tissue in endoscopic operative procedures is reduced, endoscopic operative procedures can be expanded to many areas due to the savings in time associated with the present invention, ligating anatomical tissue can be accomplished manually with thumb or squeezing action of one of the surgeon's hands or automatically by release of an operating member, where thumb action is utilized to form a ligature, the thumb action can be followed by the squeezing action to obtain additional tightening of the ligature with controlled tension, a cutter can be integrated into the ligating instrument thusly eliminating the need for extraneous cutting instruments introduced through separate portals, ligature material can be pulled through the ligating instrument and a cutter for cutting the ligature material can be actuated with a single hand and, through the use of locking mechanisms on the ligating instrument, tightening of the ligature loop around anatomical tissue and cutting of the ligature material can be prevented until optimal positioning and tightening of the loop is assured, respectively, the size of a ligature loop can be increased and reduced with one hand operation of the ligating instrument, with the ligating instrument, a ligature loop can be reduced in size to facilitate introduction through portal sleeves and increased in size thereafter to be positioned around anatomical tissue and the ligating instrument can be economically manufactured to be reusable or disposable for single patient use.

These and other objects, benefits and advantages are obtained with the present invention as characterized in a ligating instrument for ligating anatomical tissue alone or in combination with a ligating device. Where the ligating instrument is used in combination with a ligating device, the instrument includes a sleeve for receiving an end of the ligating device, a handle for being grasped by the surgeon with one hand to hold the ligating device and an operating member for securing a length of ligature material extending through the ligating device, the operating member being movable by the same hand as that grasping the handle to pull the ligature material through the ligating device such that a ligature loop disposed externally of the ligating device is reduced in size or tightened around anatomical tissue. Where the ligating instrument is used alone, the instrument includes an outer member defining a lumen for passage therethrough of a length of ligature material, a handle for being grasped by a surgeon with one hand and an operating member secured to an end of the ligature material for pulling the ligature material through the outer member to tighten a ligature loop of the ligature material around anatomical tissue to form a ligature in response to movement of the operating member with the one hand. A cutter mounted within or externally of the ligating instrument includes an actuating member for being moved by the hand grasping the ligating instrument to actuate a cutting member to cut the ligature material away from the ligature leaving the ligature in place. Methods of ligating anatomical tissue in endoscopic operative procedures according to the present invention include the steps of securing a proximal end of a ligating instrument externally of the body with one hand, introducing a distal end of the ligating instrument at a surgical site within the body, positioning a length of ligature material carried by the ligating instrument around anatomical tissue, moving an operating member of the ligating instrument with the same hand as that grasping the ligating instrument to tighten the ligature material around the tissue to form a ligature and actuating a cutter of the ligating instrument to cut the ligature material away from the ligature.

These and other objects and advantages of the present invention will become apparent from the following description of the preferred embodiments taken in conjunction with the accompanying drawings wherein identical reference numbers indicate identical parts or parts providing identical functions.

BRIEF DESCRIPTION OF THE DRAWINGS

FIG. 14 is a rear view of the operating member of the ligating instrument of FIG. 13.

FIG. 15 is a broken side view of the operating member of FIG. 14.

FIG. 16 is an opposing broken side view of the operating member of FIG. 14.

FIG. 17 is a broken top view of the operating member of FIG. 14.

DESCRIPTION OF THE PREFERRED EMBODIMENTS

Figure 1:
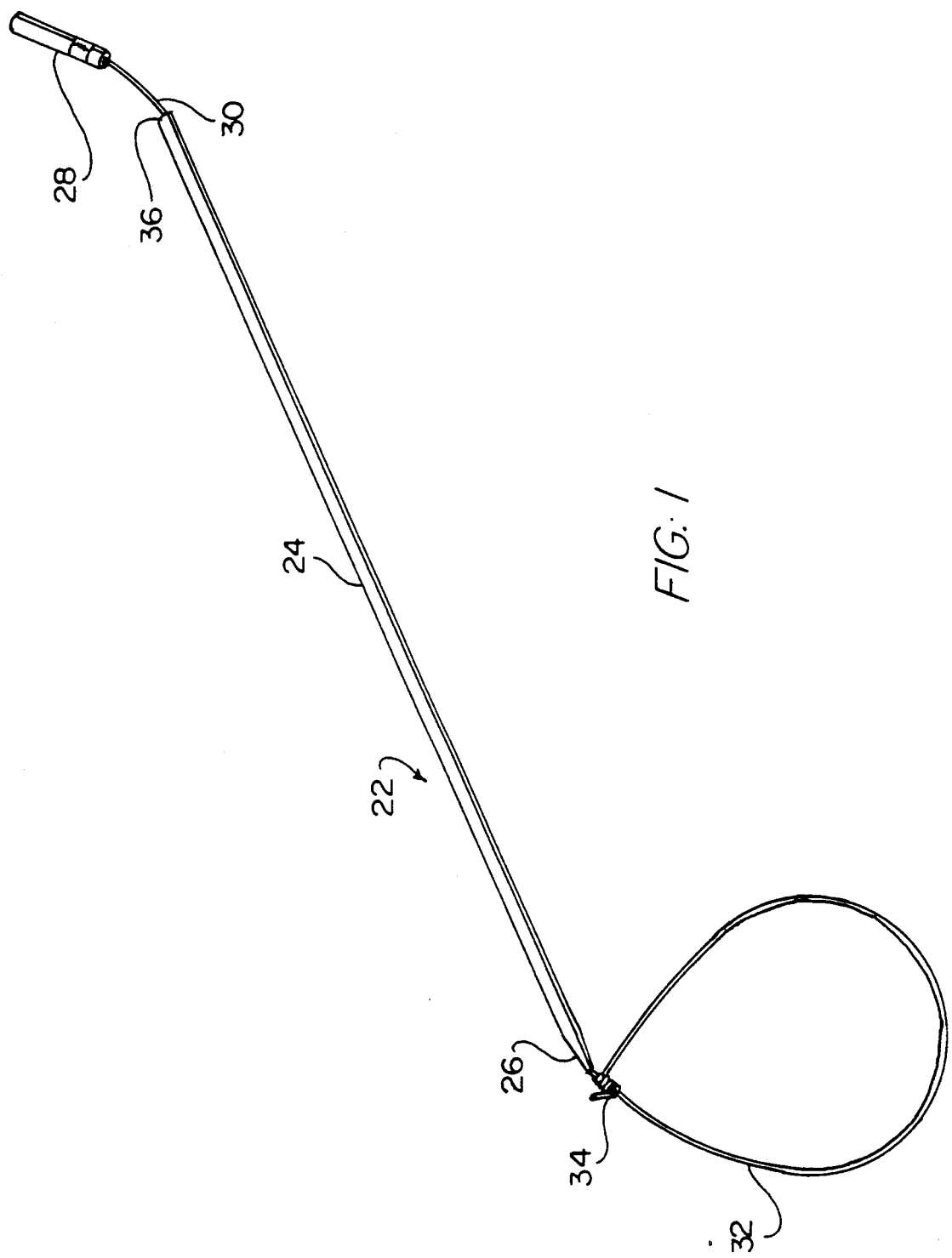
FIG. 1 is a perspective view of a ligating device with which the ligating instrument of the present invention can be used.
Figure 2:
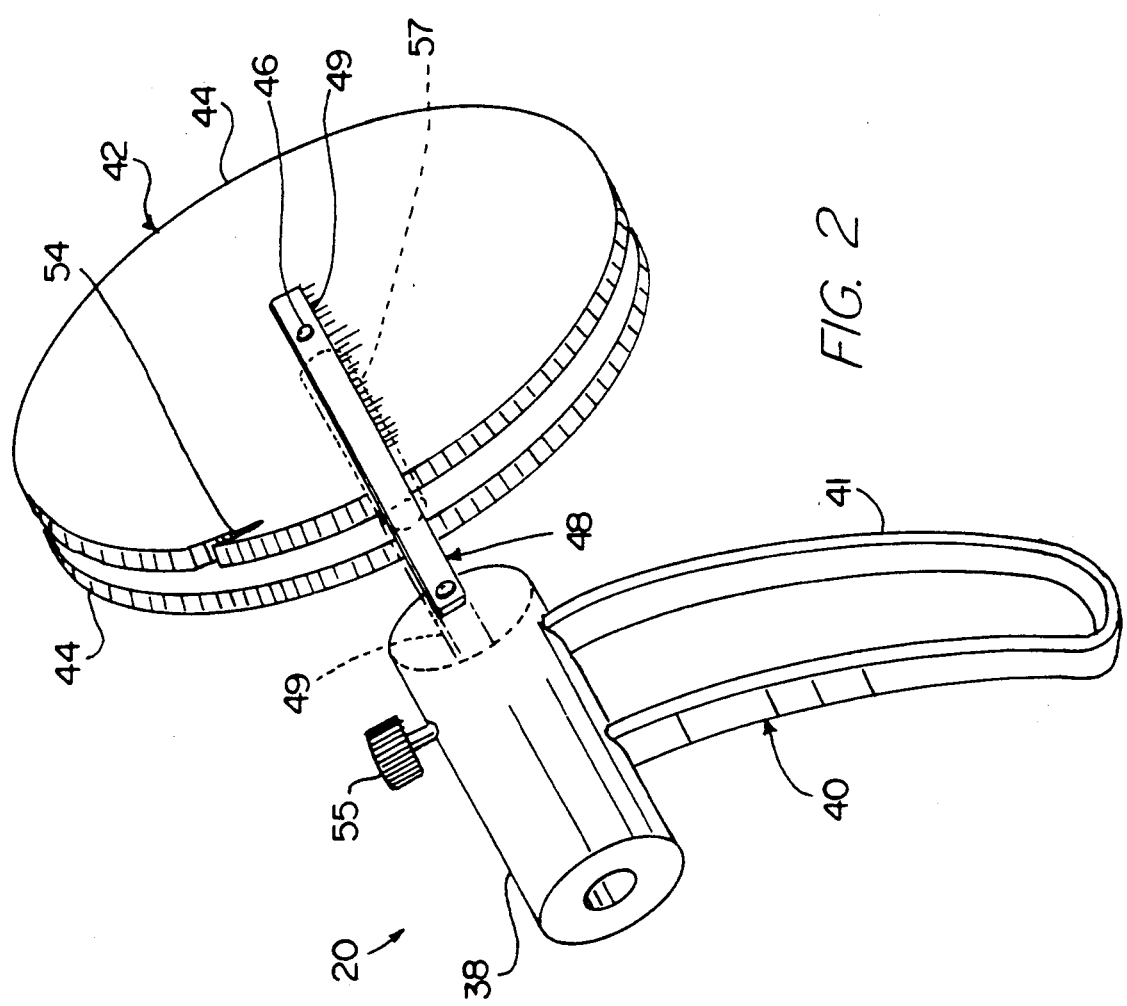
FIG. 2 is a perspective view of a ligating instrument according to the present invention.
Figure 3:
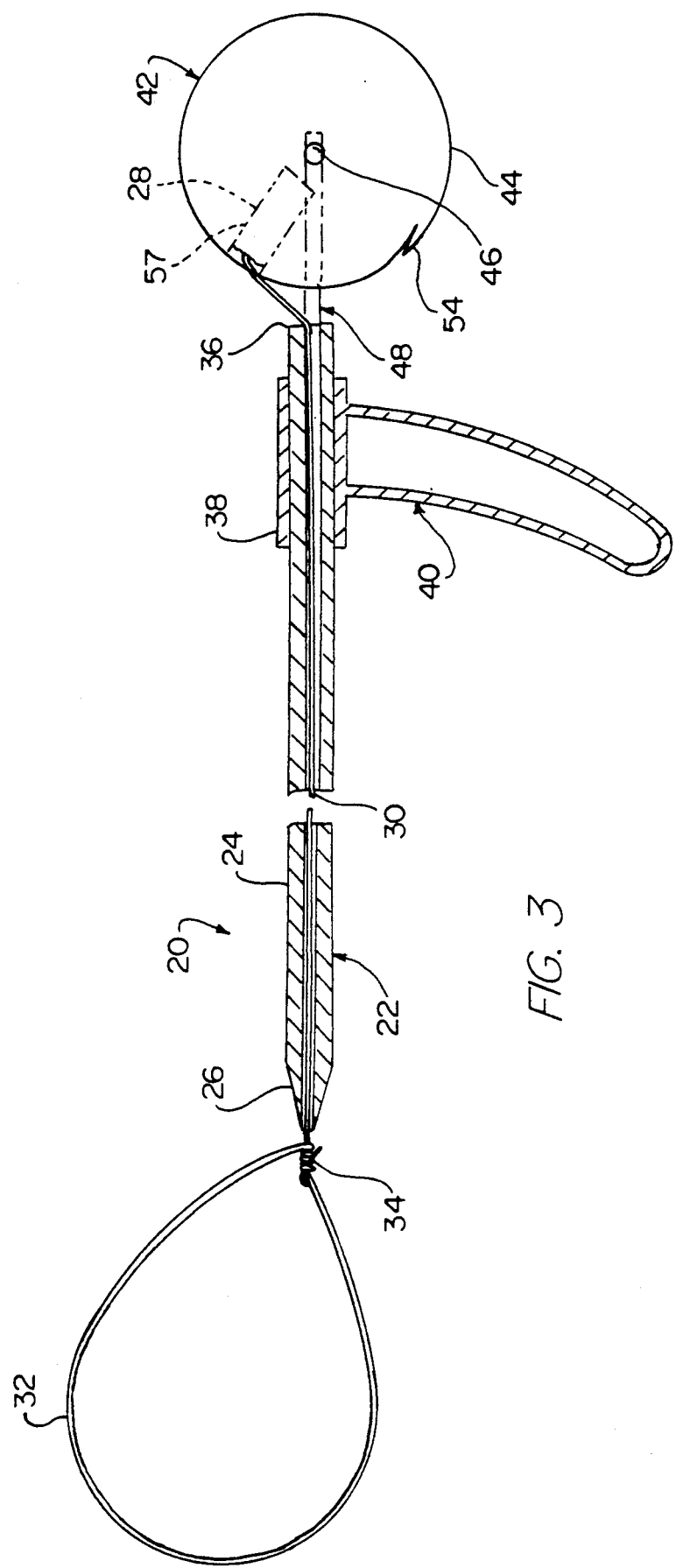
FIG. 3 is a broken side view, partly in section, illustrating the ligating instrument of FIG. 2 in use with the ligating device of FIG. 1.

A ligating instrument 20 according to the present invention is shown in FIGS. 2 and 3, the ligating instrument 20 being in the nature of an accessory or adapter for use in combination with a ligating device 22, such as the Endoloop ™ made by Ethicon, Inc. Ligating device 22, as shown in FIGS. 1 and 3, typically includes an elongate tubular member 24 having a tapered distal end 26, a proximal end 28 and a length of ligature or suture material 30 extending through the lumen of the tubular member. The ligature material 30 has an end secured to the proximal end 28 of the tubular member and is formed, externally of the distal end 26, as a ligature loop 32 for receiving anatomical tissue to be ligated. Loop 32 is made by the ligature material passing through a ligature knot 34, such as a slip or hangman's knot, formed in an end of the ligature material externally of the tubular member distal end 26. The ligature knot 34 is larger in size than the lumen of the tubular member at distal end 26 such that the ligature material can be pulled through the knot and the lumen of the ligating instrument while the knot remains held externally of the tubular member distal end to reduce the size of the ligature loop and thusly close or tighten the loop around anatomical tissue to form a ligature. The proximal end 28 of the tubular member is breakable or frangible such that the proximal end can be separated or broken off from the remainder of the tubular member at a break point 36 to permit the ligature material to be manually pulled, via the broken off proximal end, in a proximal direction through the lumen of the tubular member when forming a ligature with the loop 32. When used in endoscopic operative procedures, the ligating device 22 is introduced, typically through a portal sleeve inserted in a portal of minimal size formed in tissue of the body, at a surgical site in the body, and the loop 32 is positioned around anatomical tissue to be ligated. Operation of the ligating device 22 requires use of both of the surgeon's hands in that one hand must be used to hold the tubular member externally of the body while the other hand must be used to break off the proximal end and, via the broken off proximal end, manually pull the ligature material 30 in a proximal direction through the ligating device to tighten the loop 32 around the anatomical tissue.

The ligating instrument 20 can be used in combination with the ligating device 22 to convert the ligating device to one-handed operation and includes a sleeve 38 for receiving the tubular member 24, a handle 40 including a U-shaped handle member 41 extending outwardly from the sleeve for being grasped by a surgeon with one hand and an operating mechanism including a movable operating member 42 coupled with the sleeve 38 for pulling or drawing the ligature material 30 through the ligating device 22 in response to movement of the operating member by the surgeon's finger. Operating member 42 is in the nature of a roller or wheel including a pair of generally circular disks or plates 44 mounted in spaced relation on a spool (not shown) rotatably mounted on a pin or axle 46 secured to a mounting member 48 including a pair of mounting bars 49 which, in turn, are secured to sleeve 38, such as by screws, to couple the operating member 42 with the sleeve. Handle member 41 is configured to facilitate grasping by a surgeon with one hand while the thumb of the same hand can be utilized to engage and move the operating member. Sleeve 38 can have an inner surface sized to frictionally engage and retain the tubular member 24 of ligating device 22 and a set screw 55 can be provided in a threaded hole in the sleeve to engage and secure the tubular member therein as is useful where the outer diameter of the tubular member is smaller than the inner diameter of sleeve 38. A tube 57 can be mounted between the plates 44 in longitudinal, axial alignment with sleeve 38, the tube rotating with the operating member and having a lumen sized to frictionally engage and hold the proximal end 28 of a tubular member 24 inserted through sleeve 38. In this manner, the proximal end 28 can be broken away from the remainder of the tubular member automatically in response to rotation of the operating member as will be explained further below. Where it is not desired to break off the proximal end 28 automatically with rotation of the operating member or the tubular member is of a size too small to be held in the tube 57, the proximal end can be broken off before or after insertion of the tubular member in sleeve 38 and the ligature material 30 wrapped or wound around the spool of the operating member. A notch or slit 54 is formed in one of the plates 44 for securing a portion of the ligature material to the operating member 42 when the ligating material is wound therearound. It will be appreciated that various locking devices or latches, such as set screws, can be used on tube 57 for securing tubular members that are too small to be frictionally engaged by the inner diameter surface of the tube.

According to a method of operation for the ligating instrument 20 in endoscopic operative procedures, the tubular member is inserted through the sleeve 38 to be frictionally retained therein with the proximal end 28 held in tube 57 as shown in FIG. 3. Where automatic separation of the proximal end is not desired, the proximal end 28 of the ligating device 22 is broken away from the remainder of the tubular member 24 at break point 36, and the broken off proximal end is grasped and utilized to wind the ligature material 30 around the spool of the operating member 42. A portion of the ligature material 30 is inserted in notch 54, the notch serving to hold or secure the ligature material to the operating member with the proximal end 28 of the tubular member serving as an enlargement further preventing disengagement of the suture material from the operating member. Where automatic separation of the tubular member proximal end is desired, the proximal end 28 is inserted in tube 57 to be held therein. The handle member 41 is grasped by the surgeon with one hand, and the distal end of the ligating device 22 is introduced at a surgical site in the body through a portal of minimal size formed in tissue of the body, the ligating device typically being introduced through a portal sleeve positioned in the portal. With the ligating device 22 held externally of the body via handle 40, ligature loop 32 is positioned around anatomical tissue to be ligated. Once the anatomical tissue to be ligated is properly positioned within the ligature loop 32, the operating member 42 is rotated by the thumb of the same hand as that grasping the handle member. Rotation of the operating member causes the ligature material 30 to be pulled or drawn in a proximal direction through the lumen of the tubular member 24 and, therefore, through the ligature knot 34, the knot being held externally adjacent the distal end 26 of the ligating device such that the loop 32 is reduced in size, tightened or closed around the anatomical tissue to form a ligature. Where the proximal end 28 was inserted in tube 57, rotation of the operating member causes the proximal end 28 to be automatically separated from the remainder of the tubular member as shown in FIG. 3. Rotation of the operating member 42 by the thumb of the surgeon's hand can be controlled to obtain a desired tension for the ligature. In the case of the instrument 20, a cutting instrument is introduced at the surgical site to cut the ligature material away from the knot leaving the ligature in place; however, various types of cutters can be mounted on the instrument 20 to be operated by the same hand as that grasping the instrument to cut the ligature material as will be explained below.

Ligating instrument 20 can be designed in many various ways to receive or mount the ligating device 22 and provide a handle to be gripped by a single hand of the surgeon for holding the ligating device externally of the body. Various components and mechanisms including mechanical latches and locks, such as set screws 55 can be used to retain the ligating device 22 on the ligating instrument 20 in addition to the frictional retention shown. The handle 40 can have various configurations to facilitate grasping by the surgeon with one hand and can include one or more than one handle member. Various types of rotatable as well as non-rotatable movable operating members can be utilized in the ligating instrument to be moved or operated by the same hand as that gripping the handle to draw the ligature material in a proximal direction through the ligating device. Where the operating member is in the form of a roller or wheel, one or more plates 44 can be utilized to mount a spool for winding the ligature material. The operating member can be mounted for movement in a single direction only to permit proximal movement of the ligature material through the ligating device while preventing distal movement of the ligature material therethrough to prevent loosening of the ligature. Various devices can be used to adapt the operating member for one-way operation, such as a ratchet and pawl arrangement. The operating member 42 can be coupled with the sleeve or the handle and various mounting members can be utilized to couple the operating member with the sleeve or handle. The ligature material can be secured to the operating mechanism in many ways in addition to the tube and notch shown. The operating member can be longitudinally aligned with the sleeve as shown or the operating member can be longitudinally, angularly or laterally offset from the sleeve. The operating member can be positioned to allow insertion of the ligating device in the ligating instrument from either a proximal or distal direction. The operating member can be rotated to separate the tubular member proximal end prior to or after introduction of the instrument at the surgical site. The ligature loop does not have to be formed prior to introduction of the ligating device at the surgical site but, rather, the ligature material can be made into a loop within the body. The ligature loop itself can be made in many ways, such as by suturing the tissue to be ligated with a needle attached to the ligature material externally of the ligating device, making a knot in the ligature material with a portion of the ligature material passing through the knot to form a loop around the tissue, cutting an end of the ligature material to remove the needle, and tightening the ligature material around the tissue in response to movement of the material through the ligating device. The sleeve, handle and mounting member can be made as one piece of unitary, integral construction or as separate pieces. The operating member can be made as one piece of unitary, integral construction or as separate pieces, and non-movable portions of the operating member can be formed integrally, unitarily with the sleeve, handle or mounting member. The ligating instrument 20 can be reusable for use with various ligating devices, or the ligating instrument can be disposable for single patient use.

Where it is desired to provide automatic rather than manual operation of the operating mechanism, the operating member 42 can be replaced with the operating member 342 illustrated in FIG. 14. Operating member 342 includes a roller or wheel and a bias device such as a spring 247 mounted, such as in torsion, to bias the roller to pull the ligature material in a proximal direction through the ligating device. A release member 248 is pivotally mounted on the operating mechanism to position a pawl 74 in engagement with a ratchet tooth 72 on the operating member to prevent rotation of the operating member and, therefore, proximal movement of the ligature material, due to the rotational bias. In use, the ligature material is secured to the operating member 342 with the operating member held by pawl 74 against movement from the rotational bias, and the ligature loop is placed around tissue. Release member 248 is pivoted to disengage pawl 74 from the ratchet tooth causing the operating member to be automatically rotated to draw the ligature material through the ligating device and tighten the ligature loop around the tissue.

Figure 4:
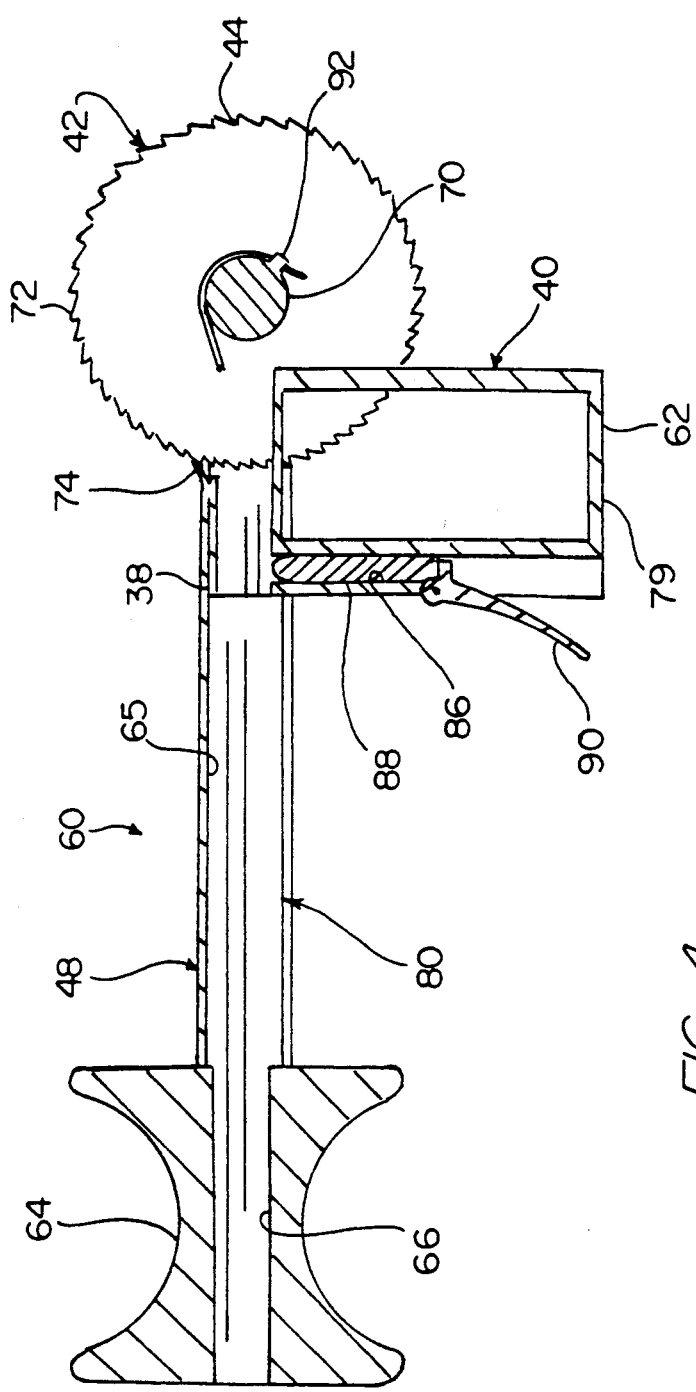
FIG. 4 is a side view, partly in section, of a modification of the ligating instrument according to the present invention.
Figure 5:
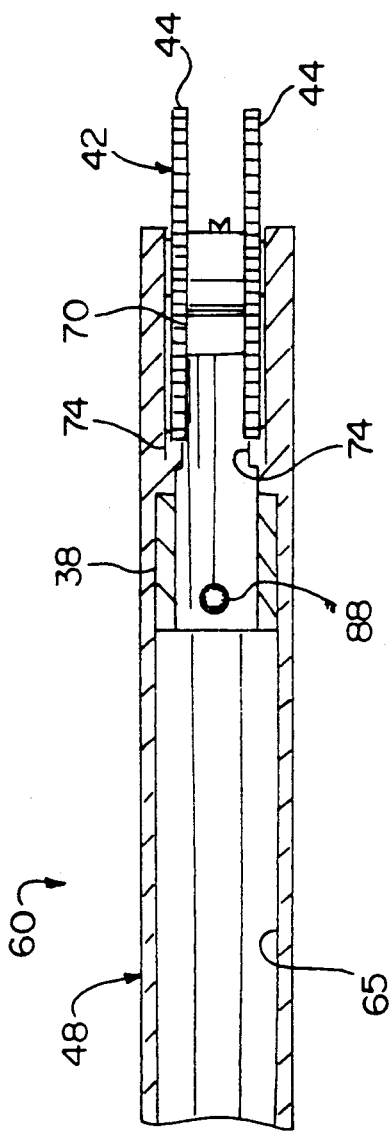
FIG. 5 is a broken top view, partly in section, of the ligating instrument of FIG. 4.

A modification of a ligating instrument according to the present invention is illustrated at 60 in FIGS. 4 and 5. Ligating instrument 60 is designed to be used in combination with a ligating device 22 and includes a sleeve 38, a handle 40 coupled with sleeve 38 and an operating member 42 for securing an end of ligature material 30 of ligating device 22. Handle 40 includes a handle member 62 and a flared hand grip 64, the hand grip being disposed distally of the handle member 62 at a distal end of a mounting member 48. Mounting member 48 can include a sleeve, as shown, connected with the operating member 42 or the mounting member can have a semicircular or any other desired configuration in cross-section, the mounting member extending longitudinally between the hand grip and the operating member. Mounting member 48 defines a longitudinal recess 65 for accommodating the tubular member 24 of ligating device 22, and the hand grip has a longitudinal passage 66 therein axially aligned with the recess of the mounting member, the diameter of passage 66 being sized to allow passage therethrough of the tubular member 24. Operating member 42 is rotatably mounted in recess 65 and is in the nature of a ratchet wheel including a pair of generally circular disks or plates 44 rigidly connected in spaced relation by a spool 70 rotatably mounted on the mounting member with the spool aligned with and extending in a direction transverse to a longitudinal axis of the instrument. Ratchet teeth 72 are disposed along the circumferences of plates 44, and the wall of the mounting member is bent or curved outwardly to form catches or pawls 74 for engaging teeth 72 to prevent rotational movement of the operating member in a counterclockwise direction looking at FIG. 4 while permitting rotational movement of the operating member in a clockwise direction. Handle member 62 includes a generally rectangular frame 79 joined to sleeve 38, the sleeve being mounted for longitudinal movement in the recess 65 of the mounting member with the frame extending through a longitudinal slot 80 in the mounting member. A forward or distal wall of the handle member has a channel 86 therein disposed at an angle with the longitudinal axis of the ligating instrument, the channel 86 communicating with the lumen of sleeve 38. A latch 88 is disposed within the channel 86 to be operated by a latch lever 90 pivotally mounted on the forward wall. The latch lever 90 is movable between an unlatched position wherein the latch 88 does not project into the lumen of the sleeve 38 as shown in FIG. 4 and a latched position wherein the latch 88 is moved by the latch lever 90 to project or protrude into the sleeve lumen and secure or squeeze the tubular member 24 of ligating device 22 therein.

According to a method of operation for the ligating instrument 60 in endoscopic operative procedures, the tubular member 24 of ligating device 22 with proximal end 28 broken away therefrom is inserted, via the passage 66 of hand grip 64 and recess 65 of mounting member 48 into the lumen of sleeve 38. The latch lever 90 is pivoted or rotated in a counterclockwise direction looking at FIG. 4 causing the latch 88 to be moved in the direction of the instrument longitudinal axis to engage or squeeze the tubular member 24 and secure the tubular member within the ligating instrument. The ligature material 30 is wrapped or wound around the spool 70, and the wall of the mounting member proximally of the sleeve can be open, as shown in FIG. 5 to provide the room necessary to wind the ligature material around the spool. A portion of the ligature material is inserted in a clip 92 on the spool and is thusly secured to the operating member 42. A tube 57 can be utilized with the instrument 60 to provide automatic separation of the tubular member proximal end. The handle member 62 is grasped by the surgeon with one hand and the distal end of the ligating device 22 is inserted at a surgical site in the body as previously described. Once the ligature loop of the ligature material 30 has been positioned around anatomical tissue to be ligated, the operating member 42 is rotated by the thumb of the same hand grasping the handle member 62 causing the ratchet wheel to rotate and pull the ligature material through the ligating device 22 to reduce the size of the ligature loop around the tissue. Teeth 72 move past the pawls 74 during clockwise movement of the operating member, the pawls 74 engaging successive teeth 72 to provide fixed, incremental positions for the operating member to facilitate precision tightening of the ligature loop while preventing movement of the ligature material through the ligating device in a distal direction and, therefore, loosening of the ligature. Once the desired final tension for the ligature has been approximated by pulling the ligature material via the operating member, the surgeon grips the flared hand grip 64 with the middle and index or other fingers of the same hand while continuing to hold the handle member 62. The surgeon then squeezes the hand, moving the operating member proximally such that the ligature material secured to the operating member is moved in a proximal direction causing the ligature to be further tightened with controlled tension. Accordingly, the operating member for the instrument 60 can be moved rotatably to approximate the final ligature and longitudinally to tighten the ligature loop with controlled tension with one hand. By providing initial reduction of the ligature loop via movement of the operating member in a rotational direction followed by additional tightening via movement of the operating member in a longitudinal direction, ligatures can be precisely tensioned with a single hand utilized to perform all steps of the ligating procedure. It should be appreciated that where the ligature loop can be tightened to the desired final tension via squeezing of the handle, the roller is not necessary.

Figure 7:
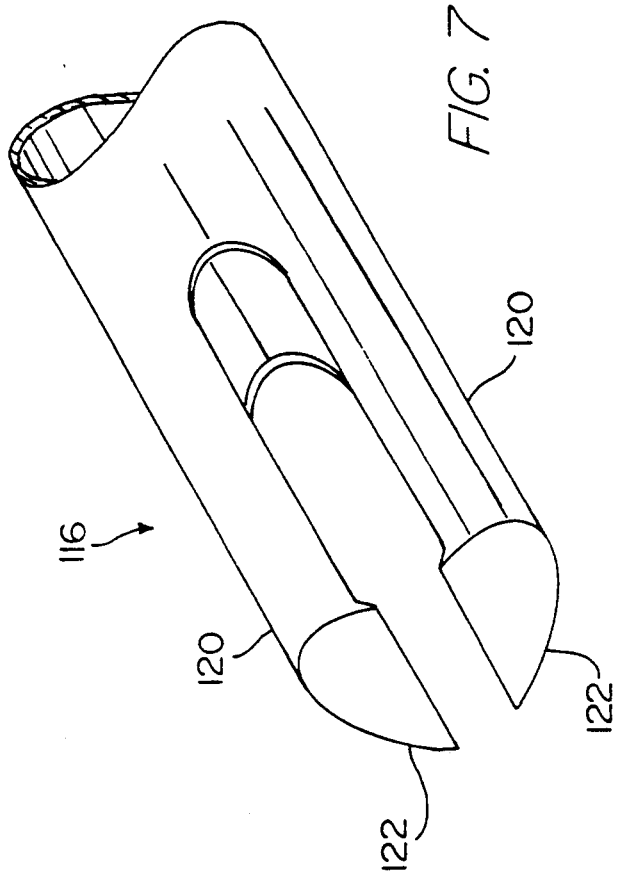
FIG. 7 is a broken perspective view of the cutter member of the ligating instrument of FIG. 6.
Figure 6:
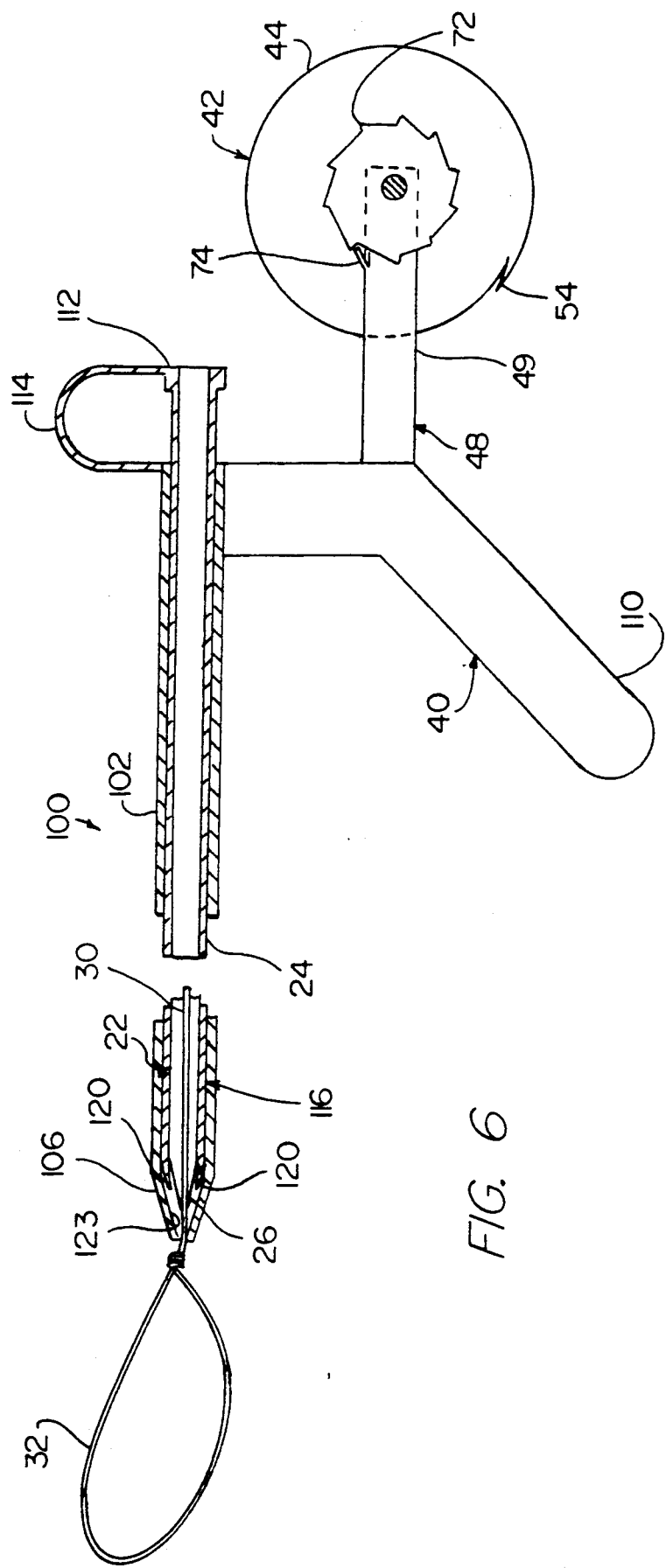
FIG. 6 is a broken view, partly in section, of another modification of the ligating instrument according to the present invention.

Another modification of a ligating instrument according to the present invention is illustrated at 100 in FIG. 6. Instrument 100 is designed for use in combination with a ligating device 22 and includes an outer tubular member 102 connected with a handle 40, an operating member 42 and a cutter 104 mounted in the lumen of tubular member 102. Tubular member 102 has a tapered distal end 106 and a proximal end coupled with handle 40. Handle 40 includes an angled handle member 110 extending outwardly from the tubular member 102 and angled toward the distal end to facilitate grasping by a surgeon with one hand. Operating member 42 is in the nature of a roller or wheel for securing an end of the ligature material 30 extending through the ligating device 22 as previously described and is coupled with handle 40 by mounting member 48 including mounting bar 49 such that the operating member is offset from and not aligned with a longitudinal axis of the ligating instrument. The operating member 42 includes plates 44 connected by spool 70 and is mounted on the mounting bar for rotation in clockwise and counterclockwise directions. Ratchet teeth 72 are disposed along the circumference of the spool at equally spaced locations therealong. A pawl or catch 74 is disposed on the mounting member to engage the teeth 72 when the operating member is moved counterclockwise such that counterclockwise movement of the operating member is limited to the arc, spacing or distance between the teeth, the pawl 74 being configured to allow movement of the teeth therepast in a clockwise direction. Cutter 104 includes as inner tubular member concentrically disposed within the outer tubular member 102 and having a proximal end extending proximally through the lumen of the outer tubular member to terminate at an actuating member 112 such as a flange, button or knob. A spring 114 is connected between the actuating button 112 and the proximal end of the outer tubular member to position a cutting member 116 at a distal end of the cutter proximally of an angled inner surface 123 of the tapered distal end 106 of the outer tubular member 102. As shown in FIG. 7, cutting member 116 includes a pair of opposing, longitudinally, distally extending cutting fingers or prongs 120 terminating at angled distal cutting blades or surfaces 122 that are moved by the angled inner surface 123 in the direction of the longitudinal axis of the instrument when the cutter is moved in a distal direction relative to the outer tubular member. The cutter 104 can be a tubular member with fingers 120 extending longitudinally, distally therefrom as shown or the cutter can be formed as a plurality of interconnected, elongate fingers or prongs extending the length of the cutter.

According to a method of operation for the ligating instrument 100 in endoscopic operative procedures, a ligating device 22 is inserted in the instrument 100 via the cutter proximal end to position the distal end 26 of the ligating device proximally of the angled surface 123. If not already broken away from the tubular member 24, the ligating device proximal end can be broken at the break point and the ligature material 30 secured thereto by slit 54, a clip or any other suitable device, or the proximal end can be inserted in a tube 57 for breaking off the proximal end automatically. Where the ligature material can be wound around the operating member several times, a securing device may not be necessary. The handle 40 is grasped by the surgeon with one hand, and the distal end 106 of the ligating instrument is introduced at a surgical site in the body as previously described. Once anatomical tissue to be ligated has been positioned within the ligature loop 32, the operating member 42 is rotated by the thumb of the hand gripping the handle to pull the ligature material through the ligating device and thusly tighten the ligature loop to form a ligature in the anatomical tissue. The ligature is tightened as desired via the operating member, and manual rotation of the operating member in the clockwise direction is stopped just prior to a tooth 72 being moved past the pawl 74. The operating member is then moved by the thumb in a counterclockwise direction until a preceding tooth is engaged by the pawl, the preceding tooth and pawl serving as a positive stop limiting counterclockwise movement of the operating member. The slack created in the ligature material with counterclockwise movement of the operating member allows the instrument to be moved proximally or backed away from knot 34. The thumb of the hand grasping handle 40 is then utilized to engage the actuating button 112 and move the cutter 104 distally relative to the outer tubular member and the ligating device against the force of spring 114 such that the fingers 120 are forced by the inner surface 123 inwardly toward the instrument longitudinal axis causing the blades 122 to cut or sever the suture material away from or proximally of knot 34 leaving the ligature in place. Accordingly, the need for a separate cutting instrument inserted through a separate portal is eliminated.

Figure 12:
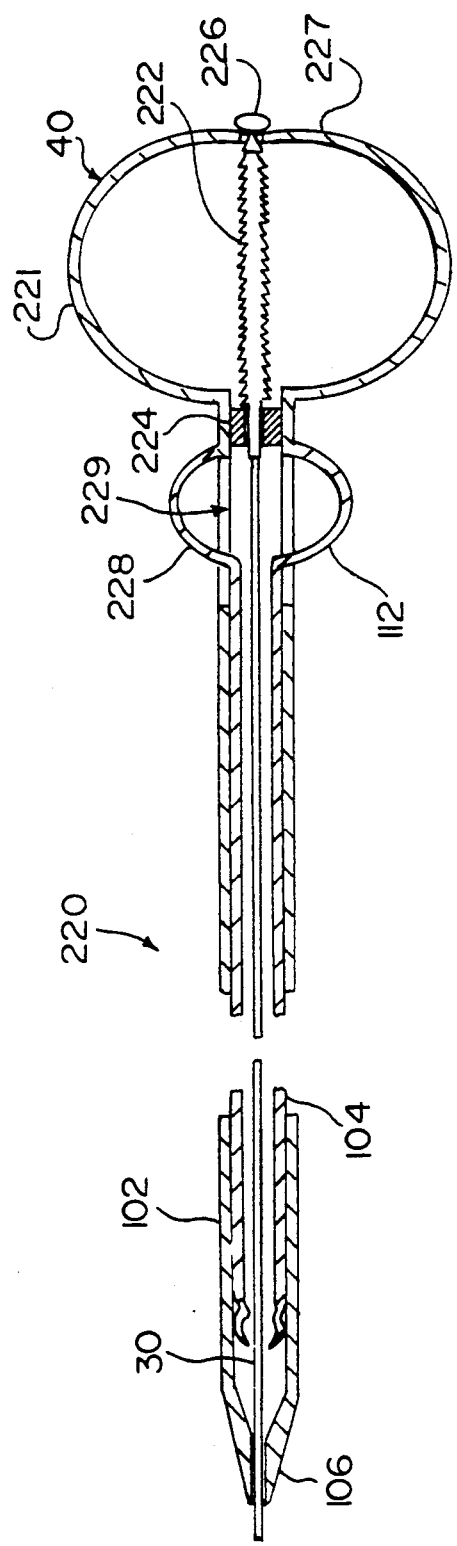
FIG. 12 is a broken side view, partly in section, of still a further modification of the ligating instrument according to the present invention.

Various types of cutters can be utilized in the instrument 100 to cut or sever the ligature material in response to movement of the cutter from a proximal end of the instrument. Various types of springs as well as other kinds of biasing devices can be utilized to position the cutting member to be engaged and moved by the outer tubular member to cut the ligature material upon movement of the actuating member. The springs or biasing devices can be arranged with the cutter and the outer tubular member in many different ways. The operating member 42 can be arranged in various angular or offset positions relative to the handle 40 and actuating member 112 to facilitate ease of operation of the operating member and actuating member by the hand gripping the handle. Various devices can be employed to limit counterclockwise movement of the operating member and, where no limit on movement of the operating member is desired, the positive stop can be eliminated. It will be appreciated that a bias device can be utilized in the instrument 100 to bias the operating member in a counterclockwise direction to create a slack in the ligature material upon release of the operating member following clockwise rotation. The actuating member can have various configurations and be mounted for movement in directions other than longitudinal, such as inwardly toward the instrument axis as shown in FIG. 12.

Figure 8:
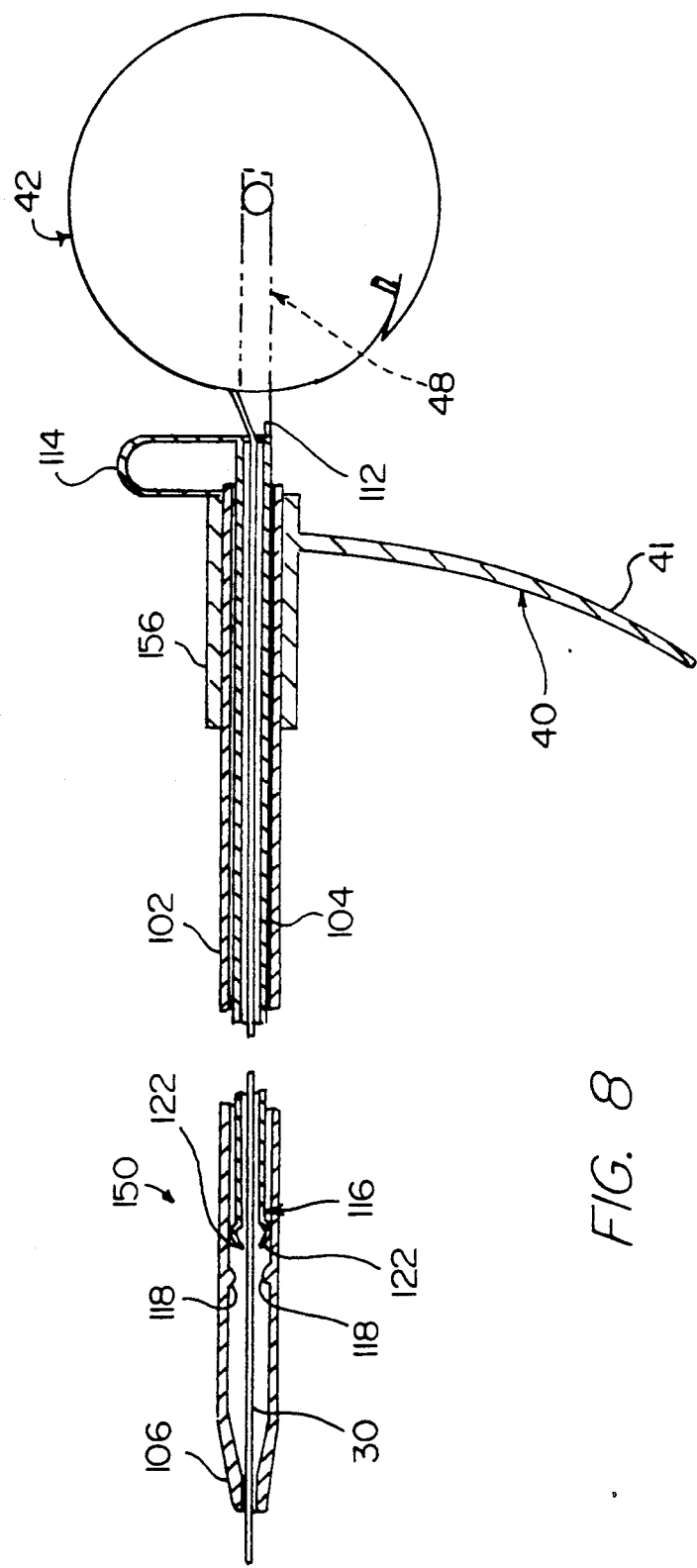
FIG. 8 is a broken side view, partly in section, of an additional modification of the ligating instrument according to the present invention.

An additional modification of a ligating instrument according to the present invention is illustrated in FIG. 8 at 150. Ligating instrument 150 is designed for use alone in ligating tissue and includes an outer tubular member 102, an operating member 42 connected by mounting member 48 with the outer tubular member, a cutter 104 disposed within the outer tubular member and a handle 40 connected with the outer tubular member. Outer tubular member 102 defines a lumen for receiving a length of suture or ligature material 30 and has a tapered distal end 106 preventing passage through the instrument of a ligature knot (not shown) of a ligature loop formed in the ligature material externally of the distal end. A proximal end of the outer tubular member is secured in a tubular flange 156 of handle 40, the flange 156 being joined to a handle member 41 extending outwardly from the outer tubular member with a curvature in a distal direction to facilitate grasping by a surgeon. The outer tubular member 102 can be secured in flange 156 in many ways including frictionally, adhesively or by locking devices and the like. By forming the handle unitarily, integrally with the outer tubular member, the flange 156 can be eliminated. Cutter 104 includes elongate fingers or prongs disposed within the outer tubular member 102 for passage therethrough by the ligature material and terminates proximally at an actuating member or end wall 112 disposed proximally of the outer tubular member proximal end. An aperture is formed in the end wall to allow passage therethrough of the ligature material 30. A spring 114 is connected between the flange 156 and the actuating member to position a cutter member 116 on a distal end of the cutter proximally of nubs or projections 118 formed on an internal surface of the outer tubular member such that angled cutter blades or surfaces 122 on the fingers of the cutter will be engaged by the nubs upon movement of the cutter distally via the actuating member. Operating member 42 is in the nature of a roller or wheel, and the roller can be rotatable clockwise and counterclockwise, one-way rotatable, biased or a ratchet wheel as previously described.

According to a method of operation for ligating instrument 150 in endoscopic operative procedures, distal end 106 is introduced at a surgical site within the body while the instrument is grasped and held, externally of the body, via handle 40 by a surgeon's one hand. The thumb of the same hand as that grasping the handle is utilized to move the operating member 42 to pull the ligature material 30 in a proximal direction through the instrument. Once a ligature is formed in anatomical tissue, the thumb of the same hand is utilized to engage the actuating member 112 and move the cutter 104 distally such that angled cutter surfaces on the cutter fingers are engaged by nubs 118 causing the cutting blades 122 to be moved inwardly toward a longitudinal axis of the instrument to sever and cut the ligature material away from the ligature knot. The cutter surfaces and the rounded nubs 118 can have various configurations to cooperate to move the cutting blades into contact with the ligature material, and the positions of the cutter surfaces and the nubs can be reversed with the cutting member provided with nubs and the outer tubular member provided with surfaces to cooperate with the nubs to move the blades into contact with the ligature material. The ligature material can be formed into a loop before or after introduction of the instrument at the surgical site, and the loop can be formed prior to the ligature material being placed around the tissue or by being placed in the tissue such as by suturing with a needle.

Figure 9:
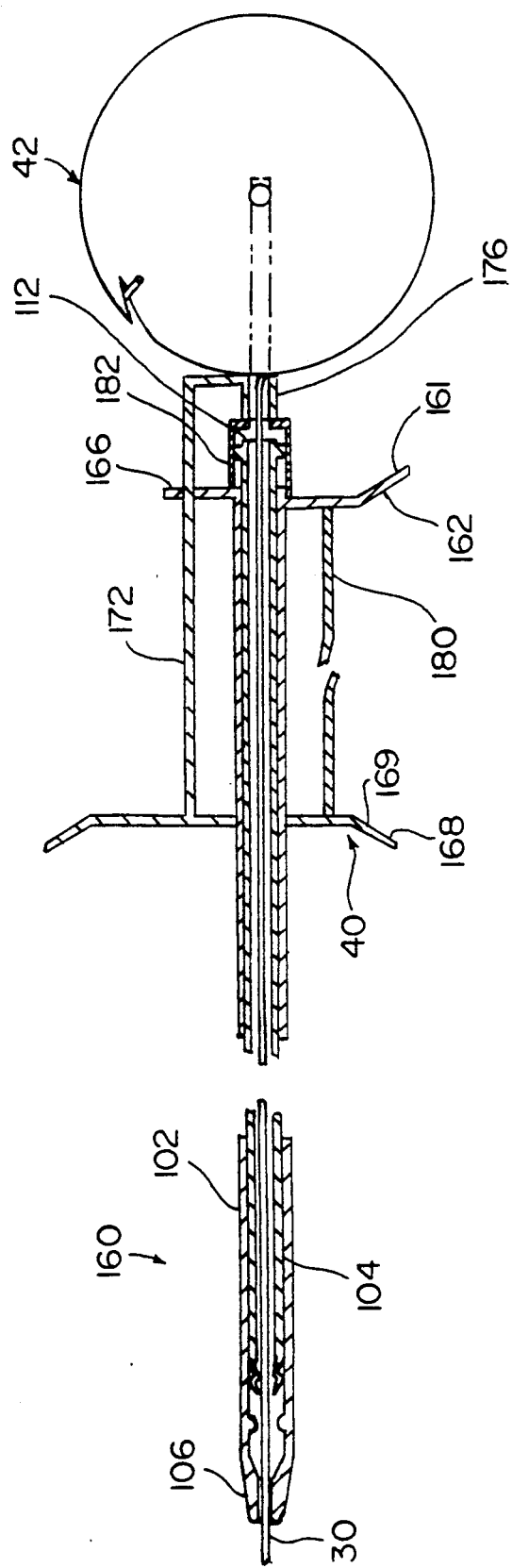
FIG. 9 is a broken side view, partly in section, of still another modification of the ligating instrument according to the present invention.

Another modification of a ligating instrument according to the present invention is shown in FIG. 9 at 160. Ligating instrument 160 is for use alone in ligating anatomical tissue and includes an outer tubular member 102, a handle 40 coupled with the outer tubular member, an operating member 42 and a cutter 104 disposed within the outer tubular member. Outer tubular member 102 defines a lumen for passage of ligature material 30 therethrough and has a tapered distal end 106 for preventing passage through the instrument by a ligature knot. The outer tubular member 102 terminates proximally at a handle member 162 of handle 40, the handle member 162 extending outwardly from the outer tubular member to define a hand grip 161 for being grasped by the hand of a surgeon and including an end wall 166 joined to the hand grip and extending outwardly from the outer tubular member diametrically opposite the hand grip. The handle member 162 can be formed integrally, unitarily as one piece with the outer tubular member or the end wall and the hand grip of handle member 162 can be formed unitarily, integrally or as separate components secured to the proximal end of the outer tubular member by any suitable means. Cutter 104 is disposed within the lumen of the outer tubular member and terminates proximally at an actuating member or flange 112 disposed proximally of the proximal end of the outer tubular member, the cutter defining a lumen or passage for passage therethrough of the ligature material. Handle 40 includes a second handle member 168 in the form of a plate having an opening therein for passage therethrough of the outer tubular member 102, the plate defining a hand grip 169 spaced distally from the hand grip 161 to be grasped, with the hand grip 161, by one hand. A connecting web 172 extends proximally from the handle member 168 through a slot in the end wall 166 and is angled toward a longitudinal axis of the instrument 160 to mount a hollow cylindrical member 176 such that the lumens of the cylindrical member, the outer tubular member and the cutter are axially aligned. The outer tubular member is slidably disposed within the opening in the handle member 168, and a locking mechanism including a frangible or breakable locking bar 180 is connected between the handle members 162 and 168 to prevent movement of the handle members relative to one another. A frangible or breakable locking strip 182 is connected between the cylindrical member 176 and the end wall 166 to similarly prevent relative movement of the handle members. By connecting the locking strip 182 with the actuating member 112, actuation of the cutter can be prevented until the locking strip is broken.

Operation of the instrument 160 in endoscopic operative procedures to form a ligature in anatomical tissue is similar to that previously described in that the handle 40 is gripped, via the handle members 162 and 168, by a surgeon with one hand and the operating member 42 is moved with the thumb of the same hand to draw the ligature material 30 in a proximal direction through the instrument. Once the ligature is formed in the anatomical tissue to approximately the desired tension, the locking bar 180 and the strip 182 are broken with the same hand that holds the handle members. The handle members 162 and 168 can be squeezed moving the operating member proximally and causing the ligature material to be drawn further in a proximal direction through the instrument for controlling the final tightening or tensioning of the ligature. Once the ligature is properly tensioned, the thumb of the same hand can be used to engage the actuating member and move the cutter 104 in a distal direction to cut the ligature material as previously described. The locking strip provides redundant protection, in addition to the locking bar, against movement of the handle members. Where redundant protection is not desired, the locking strip can be connected between the cutter and a non-movable portion of the instrument to serve as a locking mechanism for the cutter only. The locking bar and the locking strip can be mounted and secured on the instrument in many various ways to prevent movement of the handle members and cutter.

Figure 10:
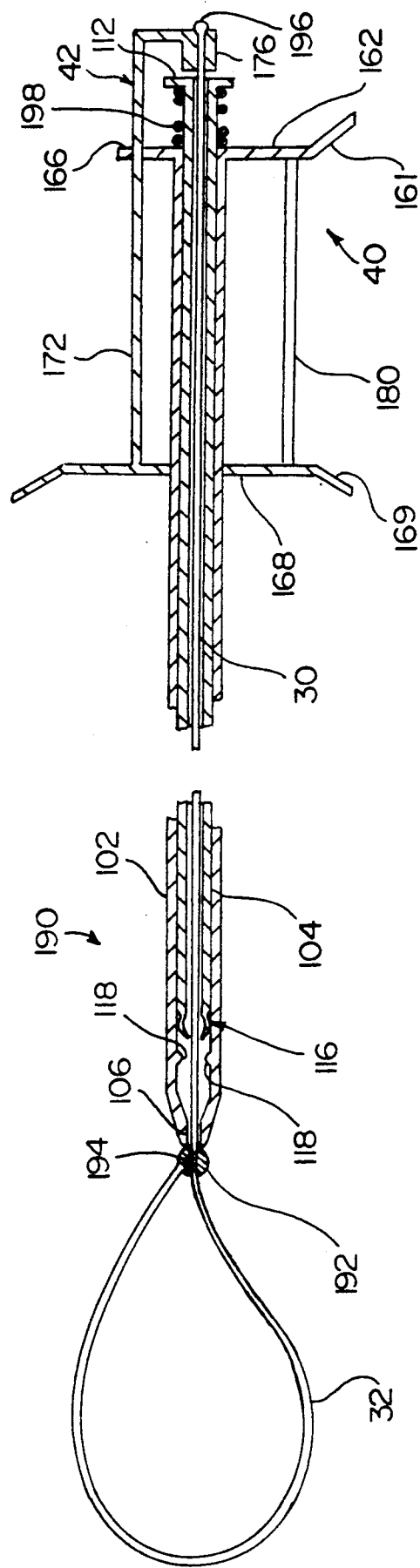
FIG. 10 is a broken side view, partly in section, of a further modification of the ligating instrument according to the present invention.

A still further embodiment of a ligating instrument according to the present invention is illustrated at 190 in FIG. 10 and includes an outer tubular member 102 coupled with a handle 40, an operating member 42 connected with an end of a length of ligature material 30 extending through the instrument and a cutter 104 disposed within the outer tubular member 102. Outer tubular member 102 defines a lumen for passage therethrough of the ligature material 30 and has a tapered distal end 106 preventing passage therethrough by a loop forming or ball member 192 performing the function of the ligature knot previously described. Ball member 192 is attached to an end of the ligature material externally of distal end 106 and has a passage for receiving a length of the ligature material to form a ligature loop 32. A plurality of protrusions 194 such as barbs or serrations extend along the passage of the ball member, the protrusions 194 being angled toward a proximal end of the instrument to prevent movement of the ligature material therethrough in a distal direction while permitting movement of the ligature material therethrough in a proximal direction to reduce the size of the ligature loop. Handle 40 includes a handle member 162 secured to a proximal end of the outer tubular member and having an end wall 166 extending outwardly from the outer tubular member diametrically opposite a hand grip 161 of the handle member. A handle member 168 of the handle 40 is in the form of a plate having an opening slidably receiving the outer tubular member for longitudinal movement therethrough. Handle member 168 defines a hand grip 169 disposed distally of the hand grip 161, and the operating member is in the form of a connecting web 172 extending in a proximal direction from the handle member 168 through a slot in the end wall 166. The operating member is angled toward a longitudinal axis of the instrument to terminate at a hollow cylindrical member 176 having a lumen axially aligned with the lumens of the outer tubular member and cutter. The ligature material 30 passes through the outer tubular member via the cutter and extends through the lumen of the cylindrical member 176 to terminate at a bump or knob 196 larger in size than the cylindrical member lumen, and the bump can be a knot, a knob or any other protrusion or enlargement disposed proximally adjacent the cylindrical member of the operating member. Cutter 104 is disposed within the outer tubular member and terminates proximally at an actuating member or flange 112 disposed proximally of the outer tubular member proximal end. A helical coil spring 198 is disposed around the cutter and is biased between the actuating flange and the handle member 162 to bias the cutter in a proximal direction such that cutter member 116 at a distal end thereof is disposed proximally of nubs 118 formed on an inner surface of the outer tubular member. A locking mechanism including a locking bar 180 hingedly mounted on one of the handle members can be provided to prevent relative movement of the handle members and, therefore, the operating member in a locked position for the locking bar, the locking bar being pivotable to an unlocked position to release the handle members and operating member for movement.

Operation of the instrument 190 is similar to that previously described in that the distal end of the instrument 190 is introduced at a surgical site in the body while being held, externally of the body, by handle members 162 and 168. Ligature loop 32 is placed around anatomical tissue to be ligated, and the handle members 162 and 168 are squeezed with one hand, causing the ligature material 30, via engagement of knob 196 with operating member 42 to be moved in a proximal direction through the instrument. Once the ligature is formed, the thumb of the same hand utilized to grip the handle 40 can be used to engage actuating flange 112 to move the cutter 104 in a distal direction to cut the ligature material. In addition to facilitating formation of the ligature loop, loop forming member 194 ensures that the loop is not increased in size or untightened during formation of the ligature. The loop forming member can have any structural configuration providing a passage for receiving the ligature material and a securement site for the end of the ligature material while preventing passage of the loop forming member into the ligating instrument.

Figure 11:
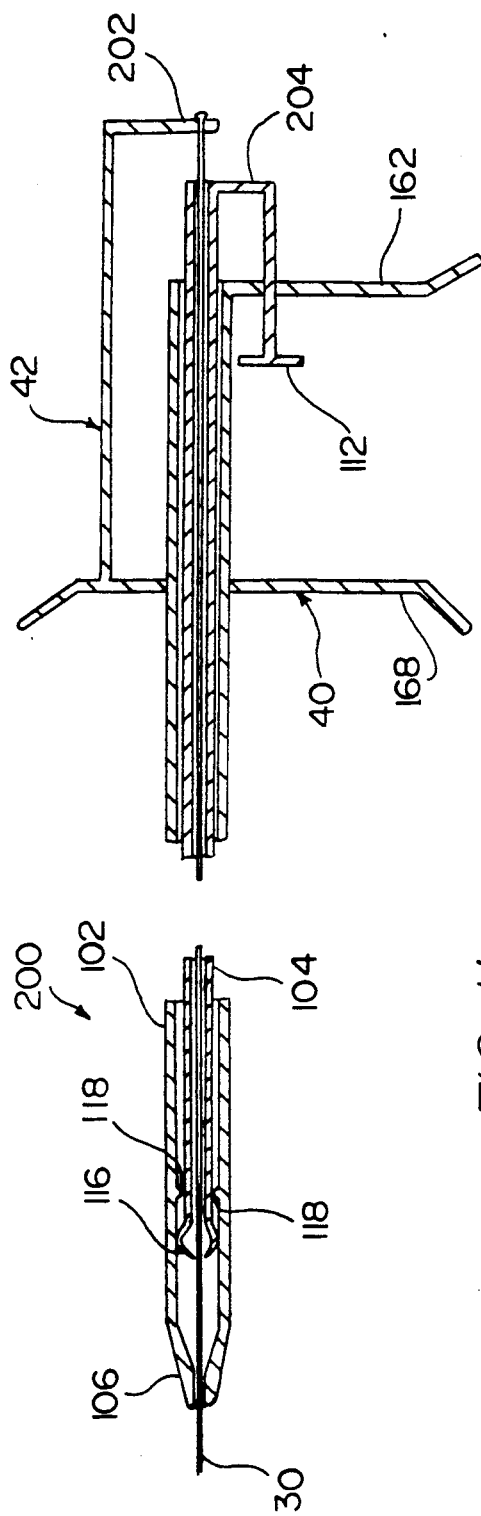
FIG. 11 is a broken side view, partly in section, of an additional modification of the ligating instrument according to the present invention.

An additional modification of a ligating instrument according to the present invention is illustrated at 200 in FIG. 11. Ligating instrument 200 includes an outer tubular member 102 defining a lumen for passage therethrough of ligature material 30, handle 40 coupled with outer tubular member 102, operating member 42 connected to ligature material 30 and cutter 104 disposed within outer tubular member 102. Outer tubular member 102 has a tapered distal end 106 preventing passage therethrough of a ligature knot or loop forming member and an open proximal end through which a proximal end of cutter 104 extends. Handle 40 includes handle members 162 and 168 extending outwardly from the outer tubular member, the handle member 168 being spaced distally from the handle member 162 to allow grasping of the handle members with one hand. Handle member 168 has an opening therein allowing passage therethrough of the outer tubular member and the operating member 42 is in the nature of a plate, strip or web of material extending proximally from the handle member 168. The operating member is bent or angled in the direction of a longitudinal axis of the instrument to terminate at an end 202 aligned with the lumens of the outer member and cutter, the ligature material 30 extending proximally through the cutter and being secured to the end. Cutter 104 has an open proximal end through which the ligature material 30 extends and a distal cutting member 116 disposed distally of nubs 118. An actuating arm 204 is angled outwardly from the cutter proximal end and bent in a distal direction to extend through an opening in the hand grip of handle member 162, the actuating arm terminating at an actuating member or button 112 disposed between the handle members 162 and 168.

According to a method of operation for ligating instrument 200 in endoscopic operative procedures, the handle 40 is grasped by the surgeon with one hand, and the distal end of the instrument is introduced at a surgical site in the body with the proximal end held, externally of the body, via the handle members 162 and 168. A ligature loop of the ligature material 30 disposed externally of the distal end 106 is positioned around anatomical tissue to be ligated, and handle members 162 and 168 are squeezed such that the ligature material is moved by the operating member in a proximal direction through the instrument to tighten the ligature loop around the anatomical tissue. Continued squeezing of the handle members results in the actuating member 112 being engaged by the handle member 168 and moved proximally thereby causing the cutter 104 to be moved in the proximal direction to be positioned by nubs 118 to cut the ligature material. The actuating member can be arranged on the instrument 200 in many various ways to be positioned in the path of movement of one of the handle members to actuate the cutter such that tightening of the ligature loop and cutting of the ligature material can be accomplished with a single motion.

A further modification of a ligating instrument according to the present invention for use alone in ligating anatomical tissue is illustrated at 220 in FIG. 12 and includes an outer tubular member 102 having a tapered distal end 106 and a proximal end terminating at a handle 40 serving as the operating member for drawing ligature material 30 through the instrument and a cutter 104 disposed within the outer tubular member. The handle 40 includes a spring 221 joined to the outer tubular member proximal end and extending proximally in a direction outwardly from a longitudinal axis of the instrument 220 with a bulging configuration. The operating member includes the spring 221 and a toothed ratchet bar 222 secured to an end of the ligature material 30, the ratchet bar being mounted in a bushing 224 disposed in the proximal end of the outer tubular member to guide movement of the ligature material. The ratchet bar extends proximally through the handle 40 to terminate at a bead 226 disposed externally, proximally adjacent the spring 221 such that the ratchet bar and, therefore, the ligature material, is moved in a proximal direction by the spring when the spring is collapsed, flattened or moved in the direction of the longitudinal axis. Cutter 104 terminates proximally at an actuating member 112 in the form of a spring 228 extending through a longitudinal slot 229 in the outer tubular member and connected between the outer tubular member and the cutter proximal end. The actuating member or spring has a bulging configuration to extend in a direction outwardly from the longitudinal axis such that the cutter is moved in a distal direction relative to the outer tubular member when the spring is collapsed, flattened, compressed or moved toward the longitudinal axis.

According to a method of operation for the ligating instrument 220 in endoscopic operative procedures, handle 40 is grasped by the surgeon with one hand, and the distal end of the instrument is introduced at a surgical site in the body to position a ligature loop disposed externally of the outer tubular member distal end around anatomical tissue to be ligated. The operating member, spring 221 in the instrument 220, is squeezed causing the spring to collapse or flatten thusly moving the ratchet bar 222 and with it the ligature material 30 in a proximal direction. Upon release of the handle 40, the spring 221 will return to the bulging configuration with an end face 227 of the spring engaging the teeth of the ratchet bar to hold the ligature material in position. The teeth of the ratchet bar can be angled toward the distal end of the instrument to prevent movement of the ratchet bar and, therefore, the ligature material, in a distal direction to prevent untightening of the ligature loop while permitting proximal movement of the ligature material. Once the ligature is formed in anatomical tissue, the actuating member, spring 228, is squeezed to collapse or flatten the spring causing the cutter to move distally to cut the ligature material.

Figure 13:
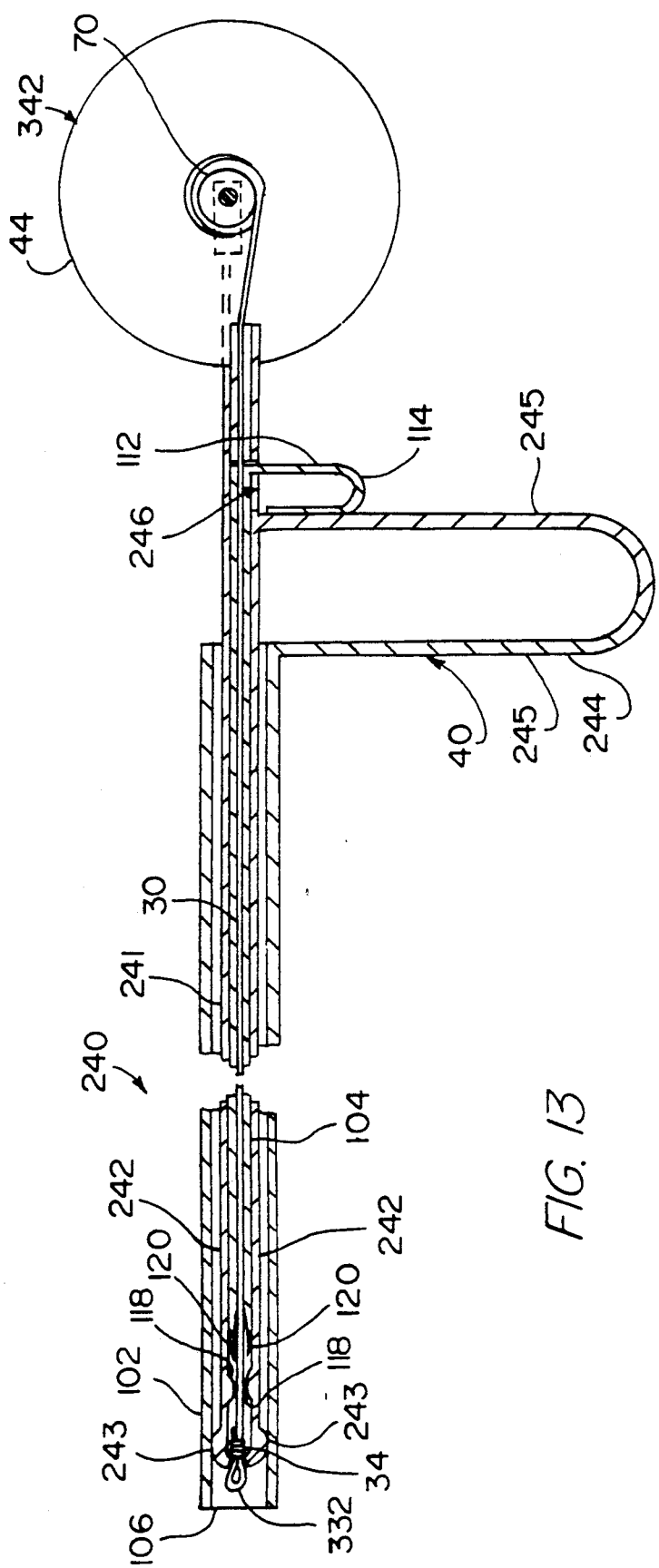
FIG. 13 is a broken side view, partly in section, of an additional modification of the ligating instrument according to the present invention.

An additional modification of a ligating instrument according to the present invention for use alone in ligating anatomical tissue is illustrated at 240 in FIG. 13 and includes an outer tubular member 102 having an open distal end 106 and an open proximal end, a middle member 241 disposed within the outer tubular member, a cutter 104 disposed within the middle member, a handle 40 mounting the middle member and a proximal end of the outer tubular member and a length of ligature material 30 extending through the instrument 240. Middle member 241 includes opposing grasping arms or prongs 242 extending longitudinally, distally to terminate at bumps 243 at a distal end of the middle member. Arms 242 are biased outwardly to an open position and are moved to a closed position via engagement of bumps 243 with an inner surface of the wall of the outer member 102 when the middle member is disposed within the outer member as illustrated in FIG. 13. Nubs 118 are disposed along an inner surface of arms 242 in opposing relation to move cutting fingers 120 of cutter 104 inwardly in the direction of a longitudinal axis of the instrument to cut ligature material 30 extending through the cutter. Middle member 241 extends through the open proximal end of the outer tubular member 102 to be disposed externally of the outer member, and handle 40 includes a U-shaped spring handle member 244 connected to the middle member 241 externally of the outer member and to the outer member proximal end. Opposing legs 245 of handle member 244 are biased to be spaced from each other as illustrated in FIG. 13 to position the bumps 243 on the middle member distal end within the outer tubular member. Cutter 104 terminates proximally at an actuating member 112 including a U-shaped spring 114 extending through a longitudinal slot 246 in the middle member 241 and connected between the cutter proximal end and the leg 245 of handle member 244 attached to the middle member. Middle member 241 terminates proximally at an operating member 342 securing an end of the ligature material extending through the instrument 240. Ligature material 30 is formed into a ligature loop 332 via a ligature knot 34, with the knot 34 being held in place within the outer member by the grasping arms 242 of the middle member as illustrated in FIG. 13. Ligature loop 332 is greatly reduced in size to be disposed entirely within the outer tubular member to facilitate introduction of the instrument at a surgical site in endoscopic operative procedures. Operating member 342 is best illustrated in FIGS. 14–17 and includes a roller or wheel having a pair of circular plates 44 rigidly mounted in spaced relation by a spool 70 around which the ligature material can be wound for securement to the operating member. Spool 70 is rotatably mounted on a pin or axle 46 secured between a pair of mounting bars 49 connected to the middle member. A bias device including a coil spring 247 is disposed around pin 46 and connected between one of the plates 44 and the corresponding mounting bar 49 as illustrated in FIGS. 14 and 15, the spring being mounted in torsion to rotationally bias the roller in a counterclockwise direction looking at FIG. 13. A plurality of ratchet teeth 72 are disposed along a side of the other of the plates 44 inwardly of the circumference thereof, the ratchet teeth being angled outwardly from the side of the plate to be engaged by a pawl 74 carried on a release lever 248 pivotally mounted on the pin 46 to prevent movement of the roller due to the rotational bias. Release lever 248 has a button for being selectively manually moved to pivot the release lever to disengage the pawl 74 from a tooth 72 permitting rotation of the roller automatically in the counterclockwise direction by the bias device. In use, ligating instrument 240 is introduced at a surgical site in the body with the ligature loop 332 held by grasping arms 242 within the outer tubular member. The ligature material 30 is wound several times around the spool 70 in a direction allowing the ligature material to be moved distally through the instrument 240 in response to manual clockwise rotation of the roller and proximally in response to counterclockwise rotation of the roller due to the torsional bias. Once a distal end of the instrument 240 has been introduced at a surgical site in the body with handle 40 held externally of the body, the thumb of the hand grasping the handle is utilized to rotate the operating member 42 in a clockwise direction looking at FIG. 13. Clockwise rotation of the operating member causes the ligature material to be moved through the ligating instrument in a distal direction while the knot 34 remains held by the middle member to increase the size of the ligature loop. The operating member is rotated until the ligature loop has been increased in size sufficiently to be placed around anatomical tissue to be ligated. When the desired size for the ligature loop has been obtained, the thumb can be removed from the operating member with pawl 74 engaging a tooth 72 to prevent counterclockwise rotation of the operating member by the bias device. The anatomical tissue is positioned within the ligature loop 332 and the button 249 of the release lever 248 is moved as shown by the arrow in FIG. 17 causing pawl 74 to be disengaged from tooth 72 such that the operating member is automatically rotated in a counterclockwise direction looking at FIG. 13 due to the bias of spring 247. With counterclockwise direction of the operating member, the ligature loop 332 will automatically be reduced in size or tightened around the tissue. Another manner in which the instrument 240 can be used involves disengaging pawl 74 from a tooth 72 prior to enlarging the ligature loop and thereafter rotating the operating member clockwise to increase the size of the loop. While holding the operating member in position with the thumb, the enlarged loop can be placed around anatomical tissue; and, thereafter, the thumb can be released from the operating member causing the operating member to be rotated automatically in a counterclockwise direction to tighten the ligature loop around the tissue.

Once a ligature has been formed in the tissue, actuating member 112 is squeezed causing the cutter 104 to be moved distally within the middle member such that cutting fingers 120 are moved by nubs 118 inwardly to cut the ligature material away from knot 34. Once the ligature material has been cut, handle 40 is squeezed drawing handle legs 245 together to move the outer and middle members relative to one another such that the distal end of the middle member is disposed beyond the distal end of the outer member. With the middle member distal end extended from the outer tubular member, the grasping arms 242 will be moved outwardly due to the outward bias causing the knot 34 to be released from the grasping arms allowing the instrument 240 to be removed from the body leaving the ligature in place. Squeezing of the handle 40 can be stopped prior to removing the instrument from the body allowing legs 245 to again position the middle member distal end within the outer member to facilitate withdrawal through a portal sleeve.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A ligating instrument for ligating anatomical tissue comprising a ligating device including an elongate body having a distal end and a proximal end and a length of ligature material extending through said body and secured to said proximal end, said ligature material being formed into a ligature loop disposed externally of said distal end for being positioned around anatomical tissue to be ligated, said proximal end being separable from the remainder of said body to allow said ligature material to be moved through said ligating device to close said ligature loop around the anatomical tissue; and an adapter including means for receiving said ligating device, a handle connected with said receiving means for being grasped by a hand of a surgeon and operating means coupled with said receiving means for securing said proximal end of said body, said operating means being movable manually by the hand grasping said handle to move said ligature material through said ligating device to close said ligature loop and form a ligature in the anatomical tissue.

2. The ligating instrument as recited in claim 1 wherein said operating means includes a rotatable operating member for being manually rotated by a finger of the hand grasping said handle.

3. The ligating instrument as recited in claim 2 wherein said rotatable operating member includes a roller.

4. The ligating instrument as recited in claim 3 wherein said roller is manually rotatable in a single direction.

5. The ligating instrument as recited in claim 4 further including means on said roller for preventing rotation of said roller in a direction other than said single direction.

6. The ligating instrument as recited in claim 3 wherein said roller is manually rotatable in clockwise and counterclockwise directions.

7. The ligating instrument as recited in claim 6 wherein said adaptor further includes means for limiting rotational movement of said roller in one of said directions.

8. The ligating instrument as recited in claim 1 wherein said receiving means includes a sleeve.

9. The ligating instrument as recited in claim 8 wherein said sleeve includes means for engaging said ligating device body and said engaging means includes a surface of said sleeve frictionally engaging said ligating device body.

10. The ligating instrument as recited in claim 8 wherein said sleeve includes means for engaging said ligating device body and said engaging means includes a latch.

11. The ligating instrument as recited in claim 1 wherein said handle includes means for further moving said ligature material through said ligating device by the hand grasping said handle to tighten the ligature in anatomical tissue upon formation of the ligature with said operating means.

12. The ligating instrument as recited in claim 1 further including a cutter carried by said receiving means for cutting said ligature material adjacent the ligature and actuating means coupled with said handle for actuating said cutter to cut said ligature material in response to movement of said actuating means by the hand grasping said handle.

13. The ligating instrument as recited in claim 12 wherein said cutter is disposed within said receiving means.

14. The ligating instrument as recited in claim 12 wherein said cutter is disposed around said ligating device.

15. The ligating instrument as recited in claim 12 wherein said ligating device further includes a longitudinal axis and said actuating means includes an actuating member movable longitudinally along said axis.

16. The ligating instrument as recited in claim 12 wherein said ligating device further includes a longitudinal axis and said actuating means includes an actuating member movable in a direction transverse to said axis.

17. The ligating instrument as recited in claim 1 wherein said adaptor further includes means for separating said ligating device proximal end from said remainder of said ligating device body automatically in response to movement of said operating means.

* * * * *